(12) United States Patent
Van Der Wal

(10) Patent No.: US 6,884,331 B1
(45) Date of Patent: Apr. 26, 2005

(54) METHOD FOR DEPOSITING AN ADHESIVE PVC LAYER ON AN ELECTRODE AND ELECTRODE OBTAINED ACCORDING TO SAID METHOD

(75) Inventor: Peter Douwe Van Der Wal, Neuchâtel (CH)

(73) Assignee: Universite de Neuchatel, Neuchatel (CH)

( * ) Notice: Subject to any disclaimer, the term of this patent is extended or adjusted under 35 U.S.C. 154(b) by 0 days.

(21) Appl. No.: 09/958,732

(22) PCT Filed: Apr. 10, 2000

(86) PCT No.: PCT/CH00/00250

§ 371 (c)(1),
(2), (4) Date: Oct. 12, 2001

(87) PCT Pub. No.: WO00/62944

PCT Pub. Date: Oct. 26, 2000

(30) Foreign Application Priority Data

Apr. 16, 1999 (FR) ............................................. 99 0496

(51) Int. Cl.$^7$ .................... G01N 27/333; G01N 27/414; B05D 3/02
(52) U.S. Cl. .................... 204/418; 427/387; 427/388.1; 257/253
(58) Field of Search .......................... 257/253; 427/379, 427/384, 387, 388.1; 502/101; 204/403.01–403.14, 416–419, 431; 156/329, 331.2–331.7

(56) References Cited

U.S. PATENT DOCUMENTS

| 4,228,061 A | 10/1980 | Plueddemann | ......... 260/31.2 R |
|---|---|---|---|
| 4,341,686 A | 7/1982 | Chakrabarti et al. | ........ 427/244 |
| 4,385,274 A * | 5/1983 | Shimada et al. | ........... 324/71.6 |
| 5,637,642 A * | 6/1997 | Boden et al. | ................ 525/104 |

FOREIGN PATENT DOCUMENTS

| DE | 1494534 | 12/1969 | ............ C09D/3/76 |
| DE | 2432006 | 2/1975 | ............. C08F/8/42 |
| GB | 1113635 | 5/1968 | ........... C08F/29/18 |
| JP | 61114156 | 5/1986 | .......... G01N/27/30 |

OTHER PUBLICATIONS

Fiaz M., et al: "Silane Crosslinking of Plasticized Poly (Vinyl Chloride)" Advance in Polymer Technology, GB, John Wiley and Sons, Chichester, vol. 17, No. 1, pp. 31–51 XP000732737 ISSN: 0730–6679, 1998.

* cited by examiner

Primary Examiner—Alex Noguerola

(57) ABSTRACT

The invention relates to a method for depositing an adhesive PVC copolymer layer on a substrate, characterized in that it comprises the following steps: formation of a mixture of copolymer precursors in an organic solvent, whereby said mixture comprises PVC and 0.1–2 wt. % organotrialkoxysilane of formula $H(HN-R_1)_x-R_2-Si-(OR_3)_3$, wherein $R_1$ and $R_2$ are alkyl groups or intermediate aromatic groups, $R_3$ is an aryl group, the three substituents $R_3$ cannot be the same and x is 0–2; a layer of said mixture is deposited on the substrate; the mixture is dried in order to evaporate the solvent; the aggregate thus obtained is heated to a temperature of 70–170° C. for a duration that respectively ranges from 3 hours and 5 minutes.

17 Claims, 1 Drawing Sheet

Figure 1:
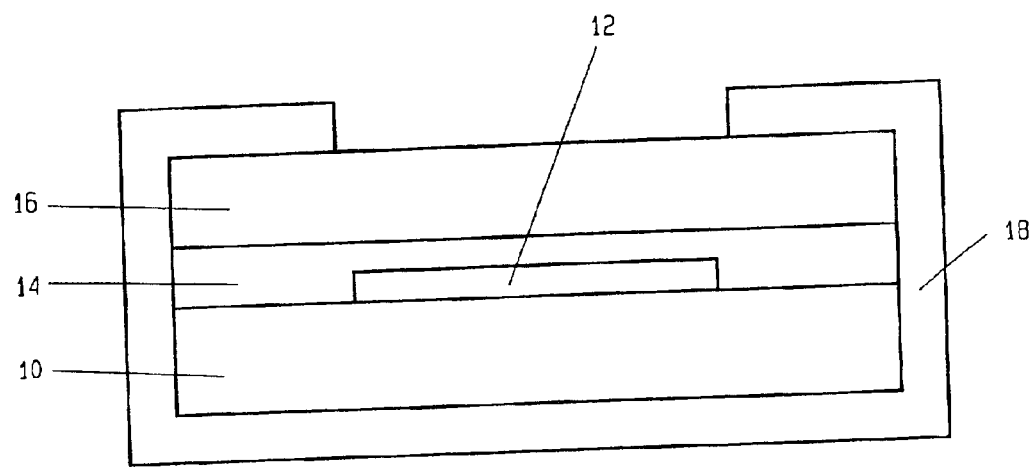

METHOD FOR DEPOSITING AN ADHESIVE PVC LAYER ON AN ELECTRODE AND ELECTRODE OBTAINED ACCORDING TO SAID METHOD

This application is a national state application under 35 U.S.C. 371 of PCT/CH00/00205 which was filed on Apr. 10, 2000.

The present invention concerns a method for depositing an adhesive layer of a copolymer of polyvinyl chloride (PVC), notably on a hydrophilic material, and even more specifically, on a material liable to react with an alkoxysilane. The invention also concerns an ion selective measurement electrode, incorporating an adhesive layer produced by this method.

The present invention refers more specifically to a method for depositing an adhesive PVC copolymer layer on an ion selective measurement electrode, of a type incorporating a substrate, an instrument designed to measure the activity of an ion in a solution and a membrane covering said instrument and formed of a PVC-base material incorporating an ionophoretic agent selected as a function of the ion to be measured.

PVC is a polymer having numerous applications. Unfortunately, bonding it to certain substrates poses a problem. This is the case, in particular, for ceramic, silicon and plastic substrates, which are hydrophilic, whereas PVC is hydrophobic.

U.S. Pat. No. 5,637,642 proposes a solution to this problem using a copolymer consisting of PVC and substitute alkyl trialkoxysilane, prepared by nucleophilic substitution at room temperature. The copolymer is placed in solution in an aprotic solvent, deposited on the substrate and then dried, again at room temperature. Such a copolymer is, it is true, interesting, but the synthesis process proposed in this patent is exceptionally laborious and demands very strict production conditions, requiring the use of inert gas, the exclusion of water, and work in the dark.

The main purpose of the present invention is to propose a simple, effective method for bonding an adhesive PVC layer for less cost on a substrate having a hydrophilic surface.

The method according to the invention is characterized in that it comprises the following steps:

Formation, in an organic solvent, of a mixture of precursors of the copolymer incorporating PVC and 0.1% to 2% by weight of an organotrialkoxysilane corresponding to the formula:

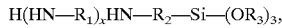

where $R_1$ is an intermediate alkyl or aromatic group, $R_2$ is also an intermediate alkyl or aromatic group, $R_3$ is an alkyl group, the three $R_3$ substituents may be not the same, and x is in the range between 0 and 2.

Deposition of a layer of this mixture on the substrate.

Drying of the mixture to evaporate the solvent, and

Heating of the aggregate thus obtained to a temperature in the 70° C. to 170° C. range, for a time ranging between 3 hours and 5 minutes respectively.

Surprisingly, and despite the small thicknesses involved, it was observed that by performing polymerization of the copolymer directly on the substrate and at a relatively high temperature, a perfectly adhesive layer is obtained for a lower cost.

It is true that methods for depositing a PVC layer on a substrate are already known. Such methods are, for example, described in documents DE 14 94 534, GB 1 113 635, EP 0 045 396 and FR 2 438 076. In these documents, a similar method is used to apply a PVC layer on a metal substrate, generally steel. The layers applied are thick, so as to protect the metal surface.

It is preferable to select organotrialkoxysilane from 3-amino propyl triethoxysilane, 3(2-aminoethyl amino) propyl trimethoxysilane, trimethoxysilyl propyl diethylene triamine or their mixture. As a variant, organotrialkoxysilane can be formed of a mixture of 3(2-aminoethyl amino) propyl triethoxysilane and phenyl triethoxysilane.

The tests performed showed that it was very beneficial to have a temperature close to 120° C. and applied for approximately two hours.

The quality of the PVC layer depends, in particular, on its flexibility. This characteristic is obtained thanks to the fact that the mixture of copolymer precursors includes, in addition, a plasticizer, in a proportion by weight of up to two parts plasticizer for one part PVC. Preferably, this proportion is one part PVC for one to two parts plasticizer.

The plasticizer can be chosen from dibutyl phthalate, bis(2-ethylhexyl) phthalate, dibutyl sebacate, bis(2-ethylhexyl) sebacate, tris(2-ethylhexyl) trimellitate, tris(2-ethylhexyl) phosphate, dioctyl phenyl phosphonate, 2-nitrophenyl octyl ether, bis(1-butyl pentyl) decane-1,10-diyl diglutarate, tetraundecyl benzophenone-3,3',4,4'-tetracarboxylate and their derivatives.

The choice of solvent depends on the type of PVC used. With a PVC of high molecular weight, the solvent should preferably be selected from methyl cyclohexanone, dimethyl formamide, nitrobenzene, isophorone, mesityl oxide, tetrahydrofurane and cyclohexanone. When a PVC of lower molecular weight is used, the solvent should preferably be selected from dipropyl ketone, methylamylketone, methyl isobutyl ketone, acetonylacetone, methyl ethyl ketone, dioxane, methylene chloride and their derivatives.

It is important that the mixture should be suitably viscous to be able to be deposited on the substrate. Good results were obtained with one part copolymer precursors for one to thirty parts of solvent. Preferably, the mixture contains one part copolymer precursors for ten to twenty parts solvent.

PVC is used in particular as an ion selective membrane designed to equip ISE type electrodes (Ion Selective Electrodes). Such electrodes can be used, for example, to measure the activity of ammonium, calcium, chloride, fluoroborate, nitrate, perchlorate and potassium ions, and to measure the hardness of water.

The membrane is generally formed of a mixture of high-molecular-weight PVC and a plasticizer, in a ratio of approximately 1 to 2, to which is added an ionophoretic agent. The latter, which performs selective conduction of ions, is formed either of an ion exchanger or a neutral transporter, in a proportion not exceeding 1% by weight. The mixture can, moreover, be supplemented by adding lipophilic salts, selected according to the electrode, the electrolyte and the application.

The use of PVC for manufacturing such membranes has proved especially effective with large-sized electrodes, offering optimum measuring conditions.

The use of a so-called planar technology permits a considerable reduction in the size of the electrode, which comprises a polymer, ceramic or doped single-crystal silicon substrate, supporting a measuring instrument produced by thin or thick layer deposition. This measuring instrument can be formed of either a layer of metal or an ion-sensitive field effect transistor (ISFET). It is preferable for the electrode to be encapsulated in epoxy, with the exception of the measuring instrument which is covered by an ion selective membrane.

This reduction in size permits a considerable reduction in the volume of solution to be analyzed. However, the bonding of a membrane, especially a PVC membrane, poses a problem.

Another aim of the present invention is to produce an ion selective electrode provided with a PVC membrane.

With an initial production method, such an electrode comprises a substrate, an instrument designed to measure the activity of an ion in a solution, and a membrane covering the measuring instrument and formed of a PVC-base material incorporating an ionophoretic agent selected as a function of the ion to be measured. According to the invention, this electrode also incorporates a layer of a PVC and organotrialkoxysilane copolymer produced by the method defined above, inserted between the substrate and the membrane, to ensure adhesion of the membrane.

Tests have shown that the membrane could be bonded directly onto the measuring instrument. With a second production method, the electrode comprises a substrate, an instrument designed to measure the activity of an ion in a solution, and a membrane covering the measuring instrument and formed of a PVC-base material incorporating an ionophoretic agent selected as a function of the ion to be measured. According to the invention, this material is a PVC and organotrialkoxysilane copolymer produced by the method outlined above.

The measuring instrument can be formed of either an ISFET or a metallic layer.

Figure 2:
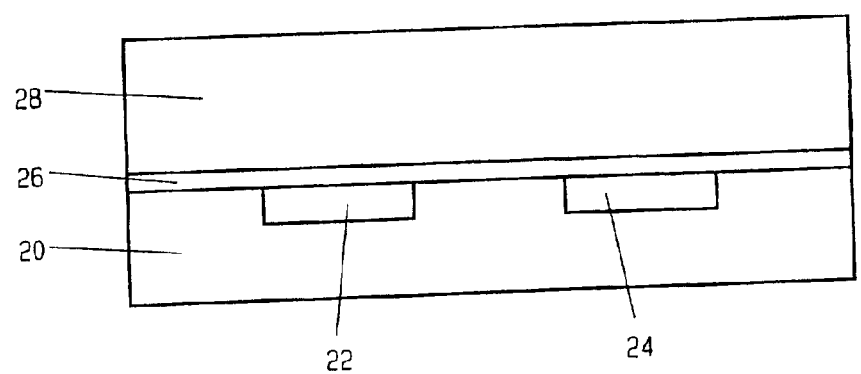

Other characteristics and advantages of the invention will appear from the following description, making reference to the appended drawing, in which FIGS. 1 and 2 represent cross-section views of electrodes incorporating, as measuring instrument, a metallic layer and an ISFET respectively.

FIG. 1 shows an electrode incorporating a substrate 10, preferably of alumina, which carries a measuring instrument 12 formed, conventionally, of a layer of silver and silver chloride. The whole is covered with an adhesive layer 14, itself coated with a membrane 16 the characteristics of which will be specified further on. An epoxy encapsulation, 18, protects the electrode, leaving merely a window opposite measuring instrument 12.

The substrate 10 could also be made of another material than alumina, e.g. glass, silicon or a plastic material preferably consisting of a polymer reacting with the amine groups, especially polyamides and epoxy resins.

FIG. 2 shows another type of electrode in which the measuring instrument is formed of an ISFET incorporating, in known manner, a substrate of single-crystal silicon 20, a source 22, a drain 24 and a gate 26. The latter is coated with a membrane 28, self-adhesive, as will be seen later. The ISFET can be mounted on a PC board and coated with epoxy, with the exception of the measurement surface. The surface of gate 26, which constitutes the sensible part of the measuring instrument, is generally formed of an oxide or nitride, e.g. a silicon dioxide, an aluminium or tantalum oxide, or again a silicon nitride.

Note that an intermediate adhesive layer 14 (FIG. 1) or a self-adhesive membrane 28 (FIG. 2) can be used indifferently with an ISFET or with a metallic electrode possibly incorporating interdigital structures such as those used for conductometry measurements.

The construction of measuring instruments, of both the thin-layer and thick-layer metallic electrode type, and the ISFET type, is perfectly well known in state-of-the-art practice and will therefore not be described in greater detail.

The electrodes shown in the drawing are designed to determine the activity of an ion in a solution, by measuring the potential difference between the electrode and a reference electrode, when they are plunged in the solution.

As was explained above, the materials forming membranes 16 and 28 play an essential role in the quality of measurement, the best results having been obtained with PVC.

The major problem posed by the use of this material lies in how to bond membranes 16 and 28.

In accordance with the invention, in the case of an electrode as per FIG. 1, membrane 16 is bonded on substrate 10 via layer 14, which is a mixture formed of a PVC and organotrialkoxysilane copolymer with or without an added plasticizer.

More precisely, to form adhesive layer 14, one begins by producing, in an organic solvent, a mixture of precursors of the copolymer incorporating PVC and an organotrialkoxysilane. A layer of this mixture is deposited on substrate 10 which is then placed for a few hours in a location in which the atmosphere is normally moist, at room temperature. The solvent evaporates and atmospheric humidity causes (at least partial) hydrolysis of the alkoxysilane groups, so that the silane is bonded to the surface of the substrate. All this is then placed in a heat chamber, at a temperature in the range between 70° C. and 170° C., for a time which is all the longer as the temperature is lower. In these conditions, the PVC reacts with the organotrialkoxysilane to form a copolymer. As will be specified further on, the best results were obtained with a treatment for two hours at 120° C.

The organotrialkoxysilane should be able to react with both the substrate and the copolymer so as to ensure bonding between one and the other. These two conditions are met when using an organotrialkoxysilane corresponding to the formula

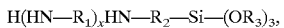

$$H(HN-R_1)_xHN-R_2-Si-(OR_3)_3,$$

where $R_1$ is an intermediate alkyl or aromatic group, e.g. an ethyl group, and $R_2$ is also an intermediate alkyl or aromatic group, e.g. a propyl, phenyl, phenoxypropyl or methyl phenyl. The three $R_3$ substituents, which may or may not be different from one another, are formed by any alkyl group, e.g. the methyl, ethyl and propyl groups. Finally, x is in the range between 0 and 2. Note that the quantity of organotrialkoxysilane corresponds to a proportion ranging between 0.1% and 2% of the total weight of the copolymer, preferably between 0.5% and 1%.

A list of plasticizers which can be used for the production of ion selective PVC membranes can be found in the "Fluka selectophore catalogue" of the firm Fluka Chemie AG, Buchs, Switzerland. Of these plasticizers, preferably use dibutyl phthalate, bis(2-ethylhexyl) phthalate, dibutyl sebacate, bis(2-ethylhexyl) sebacate, tris(2-ethylhexyl) trimellitate, tris(2-ethylhexyl) phosphate, dioctyl phenyl phosphonate, 2-nitrophenyl octyl ether, bis(1-butyl pentyl) decane-1,10-diyl diglutarate, tetraundecyl benzophenone-3, 3',4,4'-tetracarboxylate and their derivatives.

Typically, the proportion of plasticizer in the copolymer is 65%. It can be considerably lower, and even null. In the latter case, the layer obtained is very stiff.

The solvents used to dissolve the PVC and plasticizers are those generally used with PVC of high molecular weight. They include methyl cyclohexanone, dimethyl formamide, nitrobenzene, isophorone, mesityl oxide, tetrahydrofurane and cyclohexanone.

When the bonding layer is produced with PVC of lower molecular weight, preferably use a solvent chosen from dipropyl ketone, methylamylketone, methyl isobutyl ketone, acetonylacetone, methyl ethyl ketone, dioxane, methylene chloride and their mixtures.

The choice of solvent shall be made basically so that, when it evaporates, no water condensation forms on its surface. The quantity of solvent defines the mixture's viscosity, the optimum value of which depends on the method of deposition.

To produce ion selective membrane 16, use a polymer in a solution preferably formed of approximately ⅓ PVC and ⅔ plasticizer, supplemented by an ionophoretic agent, chosen according to the ions to be selected. The exact quantity of ionophoretic agent depends on the choice of materials and application.

It generally represents approximately 1% by weight of the material forming the membrane, i.e. without taking into account the solvent. The catalogue by the firm Fluka mentioned above gives all useful information concerning the choice of agent and the necessary quantity. The solvent is selected from those mentioned above. This mixture is finally spread on bonding layer 14.

In accordance with the invention, in the case of an electrode as per FIG. 2, ion selective membrane 28 is produced, directly on ISFET gate 26, in the same way as layer 14 in FIG. 1, with the sole difference that the ionophoretic agent, in that case incorporated in membrane 16, is in this case incorporated in the mixture during its preparation. It was observed, surprisingly, that such a membrane shows no major defect. Note, in particular, that ionophoretic agents withstand without any problem heat treatment at up to 170° C. without their characteristics being altered. Moreover, no sensitivity to pH, which could have been due to the introduction of an amino group, has been observed.

Various tests have been performed to test the method according to the invention.

An initial series of tests was performed to define the roles played by the choice of organotrialkoxysilane, the quantity used and the heat treatment temperature.

The basic solution was formed of 100 mg of PVC, 200 mg of dioctyl sebacate (DOS) and 3 mg of organotrialkoxysilane dissolved in 3 ml of cyclohexanone. Several types of organotrialkoxysilanes were tested, namely 3-aminopropyl triethoxysilane, 3(2-aminoethyl amino) propyl trimethoxysilane, trimethoxysilyl propyl diethylene triamine, and a mixture of 3(2-aminoethyl amino) propyl trimethoxysilane and phenyl triethoxysilane, in a proportion of 1:1 by weight.

The solutions thus obtained were spread on glass plates for microscopes to form a layer whose thickness, in the range between 50 and 100 μm, was sufficient for testing the adhesion characteristics in good conditions. The assembly was dried at room temperature during one night in a normally moist atmosphere, then heated in a furnace as indicated. The glass plates were then placed in water for at least two days.

The adhesion-related characteristics were assessed as follows:

| - | easy to remove |
| +/- | slight improvement |
| + | marked improvement |
| ++ | hard to tear off, but the layer comes off in one piece when unstuck; |
| +++ | hard to tear off, the layer is torn |
| ++++ | impossible to tear off. |

The test results are summarized in the following table.

| Type of aminosilane | Quantity [% by weight] | 70° C., 3 h | 120° C., 2 h | 170° C., 5 min |
|---|---|---|---|---|
| Without aminosilane | | - | -/+ | -/+ |
| 3-aminopropyl triethoxysilane | 0.17 | -/+ | ++ | + |
| | 0.33 | -/+ | +++ | ++ |
| | 0.66 | -/+ | ++++ | ++ |
| | 1.33 | -/+ | ++++ | +++ |
| 3(2-aminoethyl amino) propyl trimethoxysilane | 0.17 | + | ++ | + |
| | 0.33 | ++ | ++++ | ++ |
| | 0.66 | ++ | ++++ | ++ |
| | 1.33 | ++ | ++++ | +++ |
| Trimethoxysilyl propyl diethylene triamine | 0.17 | + | ++ | + |
| | 0.33 | + | +++ | ++ |
| | 0.66 | + | ++++ | ++ |
| | 1.33 | + | ++++ | +++ |
| Mixture of silanes | 0.09 | -/+ | ++ | + |
| | 0.17 | -/+ | +++ | + |
| | 0.33 | + | ++++ | ++ |
| | 0.66 | + | ++++ | ++ |
| | 1.33 | ++ | ++++ | +++ |

It is obvious that, the higher the heat treatment temperature, the shorter the treatment must be. For example, deterioration of the copolymer has been observed when the treatment exceeded five minutes at 170° C., especially with a high concentration of organotrialkoxysilane.

At a temperature of 120° C. and for the highest concentration of organotrialkoxysilane, the layer took on a yellow-brownish colour.

One observes, on examining the table, that the addition of an organotrialkoxysilane considerably increases the PVC's adhesion to glass, especially with a concentration ranging between 0.5% and 1% and heat treatment for two hours at 120° C.

It is interesting to note that tests have been performed with treatment for three hours at 80° C. The adhesion obtained before submersion in water was likewise excellent, but water droplets formed at the interface between the PVC and glass, and the number of these droplets increased sharply during the submersion.

Another test was performed using the base solution in the above example, with 1% by weight of 3(2-aminoethyl amino) propyl trimethoxysilane (relative to the total weight of PVC and plasticizer). An ISFET was coated with a fine layer (5 to 10 μm) of this mixture, then placed in a furnace at 120° C. for two hours. The layer thus obtained was covered with an ion selective layer approximately 50 μm thick, produced from a mixture formed of 100 mg of PVC, 200 mg of dioctyl sebacate (DOS) and 3 mg of an ionophoretic agent, all this being dissolved in 3 ml of cyclohexanone.

Various types of ionophoretic agents were used, namely valinomycin mixed with 0.7 mg of potassium tetrakis(4-chlorophenyl) borate, nonactin and tetradodecyl ammonium nitrate. After evaporation of the solvent in the open air for one night, the systems thus obtained were placed in an electrolyte for several hours. After this, their ion selective measurement properties were tested. The quality of the measurements was in line with expectations.

The adhesion of the layers was then checked after submersion in the electrolyte for a few days. All the parts covered with a copolymer layer showed excellent adhesion.

A third test was performed by producing a self-adhesive ion selective layer. This layer was prepared by mixing 100 mg of PVC, 200 mg of dioctyl sebacate (DOS), 0.5 mg of 3-aminopropyl triethoxysilane and 3 mg of an ionophoretic agent in 1 ml of tetrahydrofurane. The same ionophoretic agents as those mentioned above were used.

The solution thus obtained was spread on the surface of the gate of several ISFETs which had been first mounted on PC boards and encapsulated with epoxy. After evaporation of the solvent (one night in the ambient air), the ISFETs were placed in a furnace at 170° C. for five minutes, then submerged for at least two days in an appropriate electrolyte. Here again, very good adhesion was observed, and measurement results fully meeting expectations.

Thus, surprisingly, the electrodes exposed to temperatures of up to 170° C., despite the risk of decomposition of the electroactive components, gave results in every way similar to those for electrodes obtained in a known manner, with, moreover, excellent adhesion. In addition, no influence on pH was able to be detected in the regions tested, namely pH 4–9 for $K^+$ and $NO_3^-$ ions and pH 4–7 for electrodes sensitive to $NH_4^-$ ions.

What is claimed is:

1. A method for depositing an adhesive PVC copolymer layer on an electrode for ion selective measurement, the electrode comprising (a) a substrate, (b) a measuring element for measuring the activity of an ion in a solution, and (c) a membrane covering said measuring element and formed of a PVC-based material incorporating an ionophoretic agent selected as a function of the ion to be measured, characterized in that the method comprises the steps of:

forming, in an organic solvent, a mixture of precursors of the copolymer incorporating PVC and 0.1% to 2% by weight of an organotrialkoxysilane corresponding to the formula

$H(HN-R_1)_xHN-R_2-Si-(OR_3)_3,$ where:
$R_1$ is an intermediate alkyl or aromatic group;
$R_2$ is an intermediate alkyl or aromatic group;
$R_3$ is an alkyl group, with the three $R_3$ substituents possibly being not the same, and
x is in the range from about 0 to 2, depositing a layer of the mixture on said substrate,
drying the mixture to evaporate the solvent, and
heating the aggregate thus obtained to a temperature in a range from about 120° C. to about 170° C., for a time in a range from about 5 minutes to about 3 hours.

2. A method according to claim 1, characterized in that said organotrialkoxysilane is selected from 3-amino propyl triethoxysilane, 3(2-aminoethyl amino) propyl trimethoxysilane, trimethoxysilyl propyl diethylene triamine and mixtures thereof.

3. A method according to claim 1, characterized in that said organotrialkoxysilane is formed of a mixture of 3(2-aminoethyl amino) propyl trimethoxysilane and phenyl triethoxysilane.

4. A method according to claim 1, characterized in that said temperature is about 120° C. and is applied for approximately two hours.

5. An electrode for ion selective measurement, comprising (a) a substrate, (b) a measuring element for measuring the activity of an ion in a solution, and (c) a membrane covering said measuring element and formed of a PVC-base material incorporating an ionophoretic agent selected as a function of the ion to be measured, characterized in that it further comprises a layer of a PVC and organotrialkoxysilane copolymer inserted between the substrate and the membrane to ensure the latter's adhesion, and produced by the method according to claim 4.

6. An electrode according to claim 5, characterized in that said measuring element is formed of an ISFET.

7. An electrode according to claim 5, characterized in that said measuring element is formed of a metallic layer.

8. An electrode for ion selective measurement, comprising (a) a substrate, (b) a measuring element for measuring the activity of an ion in a solution and (c) a membrane formed of a PVC-base material incorporation an ionophoretic agent selected as a function of the ion to be measured, characterized in that said material is a PVC and organotrialkoxysilane copolymer produced by the method according to claim 4.

9. An electrode according to claim 8, characterized in that said measuring element is formed of an ISFET.

10. An electrode according to claim 8, characterized in that said measuring element is formed of a metallic layer.

11. A method according to claim 1, characterized in that said mixture includes, in addition, a plasticizer, in a proportion by weight of up to two parts plasticizer for one part PVC.

12. A method according to claim 11, characterized in that said proportion is one part by weight of PVC for one to two parts plasticizer.

13. A method according to claim 11, characterized in that said plasticizer is selected from dibutyl phthalate, bis (2-ethylhexyl) phthalate, dibutyl sebacate, bis(2-ethylhexyl) sebacate, tris(2-ethylhexyl) trimellitate, tris(2-ethylhexyl) phosphate, dioctyl phenyl phosphonate, 2-nitrophenyl octyl ether, bis (1-butyl pentyl) decane-1, 10-diyl diglutarate, tetraundecyl benzophenone-3,3',4,4'-tetracarboxylate and their derivatives.

14. A method according to claim 1, characterized in that said solvent is selected from methyl cyclohexanone, dimethyl formamide, nitrobenzene, isophorone, mesityl oxide, tetrahydrofurane and cyclohexanone, and that the PVC is of a high molecular weight type.

15. A method according to claim 14, characterized in that said mixture contains one part by weight of precursors of said copolymer for one to thirty parts of solvent.

16. A method according to claim 15, characterized in that said mixture contains one part by weight of precursors of said copolymer for ten to twenty parts of solvent.

17. A method according to claim 1, characterized in that said solvent is selected from dipropyl ketone, methylamylketone, methyl isobutyl ketone, acetonylacetone, methyl ethyl ketone, dioxane, methylene chloride and their mixtures, and in that the PVC is of a low molecular weight type.

* * * * *